United States Patent [19]
Chiffon et al.

[11] Patent Number: 5,591,396
[45] Date of Patent: Jan. 7, 1997

[54] SELF CLEANING DRAIN SYSTEM AND MODULAR PLUMBING SYSTEM FOR A STERILIZING APPARATUS

[75] Inventors: Mark E. Chiffon, Erie; Kenneth J. Klobusnik, Lake City; Anthony B. Ruffo, Erie, all of Pa.

[73] Assignee: American Sterilizer Company, Erie, Pa.

[21] Appl. No.: 418,786

[22] Filed: Apr. 7, 1995

[51] Int. Cl.⁶ .................................................. A61L 2/16
[52] U.S. Cl. ................... 422/26; 422/28; 422/292; 422/295; 422/296
[58] Field of Search .................... 422/26, 292, 295, 422/296, 28; 137/238, 240, 241

[56] References Cited

U.S. PATENT DOCUMENTS

| | | | |
|---|---|---|---|
| 3,371,986 | 3/1968 | Brown | 422/295 |
| 3,985,994 | 10/1976 | Eloranta et al. | 219/201 |
| 4,108,601 | 8/1978 | Wolff | 422/295 |
| 4,164,538 | 8/1979 | Young et al. | 422/26 |
| 4,203,947 | 5/1980 | Young et al. | 422/114 |
| 4,228,135 | 10/1980 | Wolff | 422/296 |
| 4,238,447 | 12/1980 | Wolff | 422/26 |
| 4,288,404 | 9/1981 | Redikultsev et al. | 422/107 |
| 4,335,075 | 6/1982 | Kackos | 422/296 |
| 4,603,114 | 7/1986 | Hood et al. | 436/89 |
| 4,759,909 | 7/1988 | Joslyn | 422/26 |
| 4,781,898 | 11/1988 | Jones | 422/295 |
| 4,808,377 | 2/1989 | Childers et al. | 422/26 |
| 4,830,278 | 5/1989 | Kohmura et al. | 99/468 |
| 4,909,988 | 3/1990 | Childers et al. | 422/26 |
| 4,915,606 | 4/1990 | Shimokawa | 422/295 |

*Primary Examiner*—Robert J. Warden
*Assistant Examiner*—Theresa T. Snider
*Attorney, Agent, or Firm*—Jones, Day, Reavis & Pogue

[57] ABSTRACT

Blockage in sterilizers due to the solidification of spilled liquid agar downstream from the sterilization chamber is prevented by heating the drain stream exiting the sterilization chamber so that the temperature of the liquid agar stays above 45°–50° C. prior to discharge from the sterilization plumbing system.

An improved modular plumbing system for sterilizers is provided, where the piping and valving requirements for a discrete operation performed by the sterilizer are segregated in a single manifold.

7 Claims, 4 Drawing Sheets

SELF CLEANING DRAIN SYSTEM AND MODULAR PLUMBING SYSTEM FOR A STERILIZING APPARATUS

FIELD OF THE INVENTION

The present invention relates to a sterilizer that prevents blockage from developing in sterilizer plumbing downstream from the sterilization chamber due to the solidification of liquid agar spilled in the chamber, by heating the stream of liquid agar draining from the sterilizer chamber. The temperature of the liquid agar is maintained in excess of 45° C. to 50° C. prior to the discharge of the liquid agar stream from the plumbing system of the sterilizer. The present invention also relates to a modular plumbing system for a sterilization apparatus that combines the piping and valve requirements for an operation of the sterilizer into a separate manifold.

BACKGROUND OF THE INVENTION

Devices for the sterilization of liquid agar using principals of heat transfer upon vapor condensation are known. In general, such sterilizers have a sterilization chamber having a drain and a door, a jacket surrounding the chamber in whole or in part, and a plumbing system of piping and valves. Heated vapor, such as steam, is introduced into the jacket and through the jacket into the chamber after any appropriate conditioning of the load has taken place. Leak-free joints and connections are necessary in order to efficiently maintain the desired pressure and temperature within the chamber and jacket during the sterilization cycle. It is therefore desirable to provide a secure seal between the sterilizer door and the sterilizer chamber throughout the sterilization cycle.

Current sterilizers use a variety of door sealing mechanisms including door seals activated by fluid under pressure. Of particular relevance to this invention are sterilizers that employ a door seal activated by pressure from the introduction of heated fluid into a door seal activation space, and having a constant bleed stream of fluid flowing out of the door seal activation space throughout the sterilization cycle when the door seal is activated. Known sterilizers employing such a door seal do not direct the door seal bleed stream into proximity with the drainage stream from the sterilization chamber in a manner causing heat to be transferred from the door seal bleed stream to the chamber drain stream.

Blockage frequently is encountered in the plumbing systems of current sterilizers during the sterilization of liquid agar. The blockage can result from spills within the sterilization chamber when sterilizing liquid agar. The spill may occur if the liquid agar boils over the edges of its container, the container breaks, or the container is upended within the sterilization chamber. Once the spilled liquid agar drains from the chamber, it cools and solidifies downstream from the chamber where there is insufficient heat to remove the blockage. Once a blockage is formed, current sterilizers are inoperable until the blockage can be located and removed.

Current sterilizers are piped using discrete components without regard to the sterilizer function served by the particular pipe, valve or joint. This plumbing system is labor intensive in manufacturing the sterilizer, and results in complexities in spacing the piping and in maintaining and servicing the sterilizer. A failure or other malfunction of a valve, pipe, joint or other component in the plumbing system causes the entire sterilizer to be inoperable until the component is repaired or replaced. Routine maintenance of the plumbing system and its components also incapacitates the sterilizer until the maintenance is completed. Current sterilizer plumbing systems also create complexities in spacing between piping that renders access to the pipes inconvenient.

There is therefore a need to develop a sterilizer that prevents blockage from the solidification of spilled liquid agar downstream from the sterilization chamber. There is also a need to develop a sterilizer that simplifies the plumbing system so that repairs and maintenance can be more easily accomplished without the necessity of incapacitating the sterilizer, and so access to the plumbing system components can be more easily achieved.

SUMMARY OF THE INVENTION

The present invention provides an improved sterilizer for preventing blockage from the solidification of spilled liquid agar downstream from the sterilization chamber. The present invention provides for heating the liquid agar downstream from the chamber so as to maintain the temperature of the liquid agar above 45–50° C. prior to its discharge from the plumbing system of the sterilizer.

The present invention also provides an improved modular plumbing configuration for a sterilizer. The piping and valving requirements for a separate operation of the sterilizer are combined in a separate manifold, to enable maintenance and repair procedures to easily proceed without necessarily incapacitating the sterilizer. A manifold is a single housing unit enclosing valving and piping requirements as desired for the specific sterilizer operation, and having inlet and outlet ports as needed. A malfunction within one manifold can be repaired by removing the manifold and replacing it with an operational manifold. The sterilizer is then able to operate while repairs are carried out on the malfunctioning manifold. The manifold also enables easier access to the pipes and valves of the sterilizer.

DETAILED DESCRIPTION OF THE INVENTION

Figure 1:
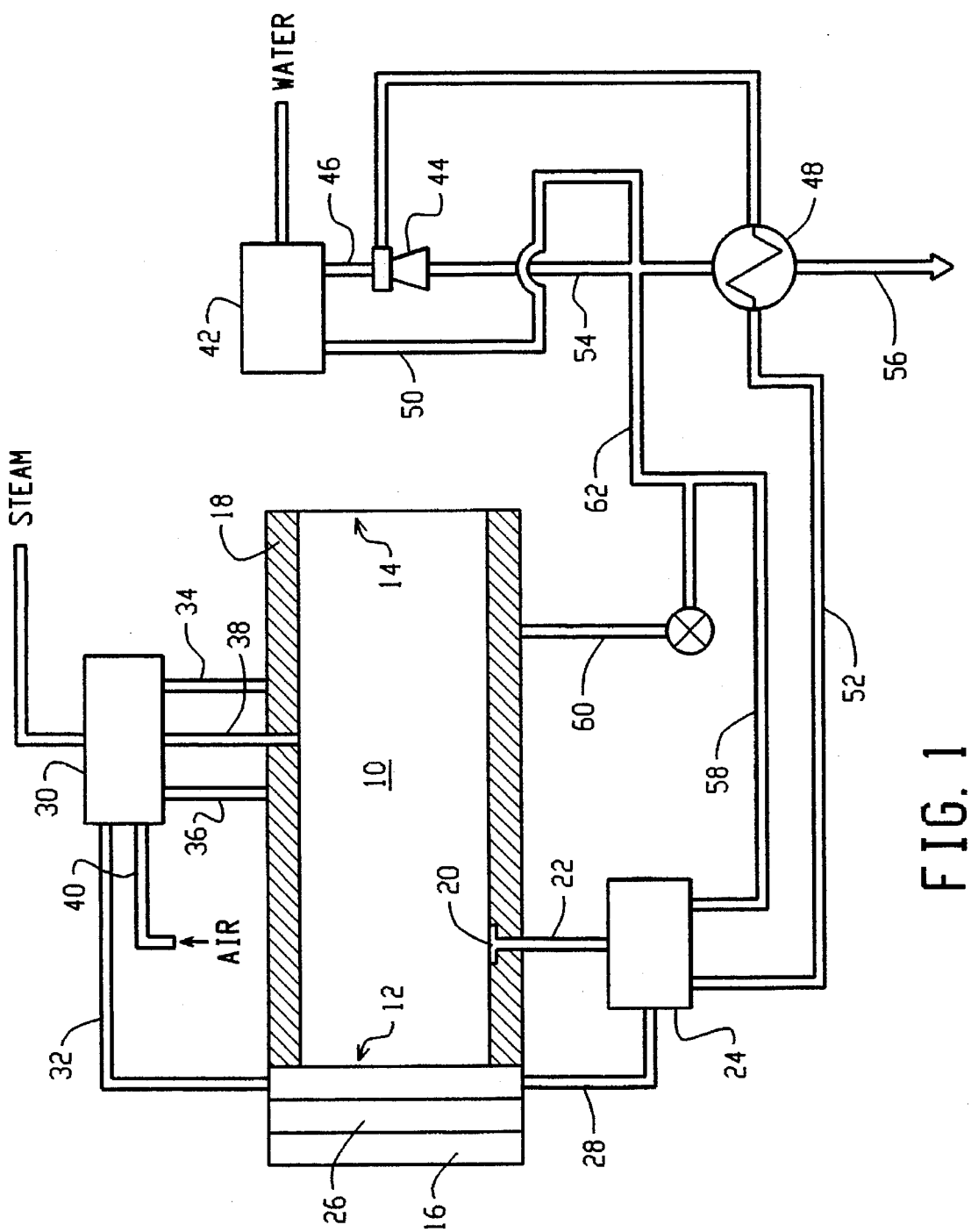
FIG. 1 is a schematic diagram of an embodiment of a steam sterilizer according to this invention.

The present invention provides a modular plumbing configuration for a sterilizer. The plumbing requirements for an operation of the sterilizer are segregated in a single manifold. A manifold can then be easily incorporated into or removed from the sterilizer without affecting the piping and valving required by other operations of the sterilizer. This modular plumbing configuration also simplifies required access to the piping and valves.

The incorporation of piping and valving requirements for a single operation into a manifold as provided in the present invention is useful for sterilizers that employ dry heat, steam heat and heat from condensed vapors as the sterilant as well as sterilizers that employ liquid and vapor chemicals as the sterilant. While an embodiment of the present invention employs steam heat as the sterilant, it should be recognized that the benefits of the modular plumbing system of the present invention are not limited to any particular sterilant, and these benefits can also be obtained if sterilants other than steam are used.

The present invention also provides for the prevention of blockage resulting from the solidification of spilled liquid agar downstream from the sterilization chamber. This benefit of the present invention requires that the drain stream of liquid agar from the chamber be heated downstream from the chamber so that the temperature of the drain stream of liquid agar is maintained in excess of 45°–50° C. until the liquid agar is discharged from the plumbing system of the sterilizer. It will be recognized by those skilled in the art that liquid agar solidifies at 45°–50° C. and that after an initial solidification, the agar does not again liquify until heated to a temperature of approximately 100° C.

It will be seen that in one embodiment of the present invention, the working fluid used to supply heat to the drain stream of liquid agar is steam at a temperature of not more than 292° F. that is used to activate the door seal of the sterilizer. It will be appreciated that alternate heat sources, including other working fluids known in the art and having a temperature above 45°–50° C. may be used to supply sufficient heat to the drain stream of liquid agar downstream from the chamber so as to maintain the temperature of the drain stream of liquid agar above 45°–50° C. prior to its discharge from the plumbing system of the sterilizer.

In this embodiment of the present invention, the drain stream of liquid agar is heated by flowing through an exhaust manifold. This drain stream flows through approximately 5 inches of piping between the chamber drain and the inlet port of the exhaust manifold. The flow of steam used to activate the door seal is at a temperature of not more than 292° F. and is directed through the exhaust manifold at a rate of approximately 15 lbs./hr in a bleed stream to control the pressure activating the door seal. The heat from this bleed stream is transferred within the exhaust manifold to the drain stream of liquid agar. The exhaust manifold is constructed of forging brass according to ASTM B 283-86 with a nominal composition of 60% copper, 2% lead and 38% zinc and has a thermal conductivity of 69 Btu/ft./hr./° F. at 68° F. One skilled in the art will recognize that the benefits of the present invention can be obtained by using other combinations of working fluid, flow rate and exhaust manifold composition known in the art to transfer sufficient heat to the drain stream of liquid agar to maintain the temperature of the drain stream above 45°–50° C. prior to its discharge from the plumbing system of the sterilizer.

For a steam heat sterilizer according to the present invention, discrete operations of the sterilizer include the supply of steam, the supply of cooling water and the supply of an exhaust system. In one embodiment of the present invention, the piping and valving requirements for each of these three operations have been separated into a steam supply manifold, a water manifold and an exhaust manifold, respectively. It will be appreciated that the benefits of the present invention can be obtained where the piping and valving requirements for less than all of the discrete operations of the sterilizer are segregated in a separate manifold.

It is contemplated that the sterilizer of this invention is equipped with suitable control means (not shown) known in the art to actuate the various valves in response to pre-determined signals and to signals generated by temperature and pressure measurements at appropriate times as set forth herein. The temperature and pressure measurement devices are known in the art and are not shown.

FIG. 1 is a longitudinal cross-section schematic diagram of a steam heat sterilizer according to this invention, comprising a steam sterilizing chamber 10 with a first end 12 and a second end 14 and a door 16 at the first end 12 which can be opened or closed for the purpose of accessing the items to be sterilized within the chamber 10. The chamber 10 is surrounded about its length with a jacket 18.

The door 16 is hinged or otherwise connected to the first end 12 of the chamber 10 using any conventional closing mechanism to enable the chamber 10 to be opened or closed, and further enabling the door 16 to be fixed in place when closed. It will be recognized that a different embodiment of the present invention employs a plurality of doors.

The base of the interior of the chamber 10 is equipped with a chamber drain 20 to enable condensate or other fluid to flow through the drain 20 and into conduit 22 that leads to the exhaust manifold 24.

The sterilizer is equipped with a door seal 26 positioned between the first end 12 of the chamber 10 and the door 16. The door seal 26 is activated prior to initiating a sterilization cycle by the introduction of steam from the steam supply manifold 30 into space between the door seal 26 and the first end 12 (the door seal activation space), creating sufficient pressure to push the door seal 26 against the door 16. The steam flows through the door seal activation space and exits into conduit 28 that leads to the exhaust manifold 24.

The sterilizer is equipped with a steam supply manifold 30. The steam supply manifold 30 receives steam from a suitable source, and directs the steam to activate the door seal 26 through conduit 32 and to the jacket 18 through conduit 34. The steam supply manifold 30 also receives steam exiting the jacket through conduit 36 and directs it to the chamber 10 through conduit 38. Steam supply manifold 30 also receives air from a suitable source through conduit 40, and directs the air to the chamber 10.

The sterilizer is equipped with a water manifold 42 to supply water to the vacuum water ejector 44 through conduit 46 and to the heat exchanger 48 through conduit 50. The vacuum water ejector 44 is a conventional venturi device useful for condensing steam and drawing vacuums, as known in the art. The heat exchanger 48 can be of any design useful to cool the steam and condensate as is known in the art. The stream exiting exhaust manifold 24 through conduit 52 passes through the heat exchanger 48, and then through the vacuum water ejector 44. This stream then flows through conduit 54 to the heat exchanger 48 and then is discharged through discharge outlet 56. The stream exiting exhaust manifold 24 through conduit 58 is joined by the stream of conduit 60. The joined stream flows through conduit 62 and joins the flow through conduit 54.

Figure 2:
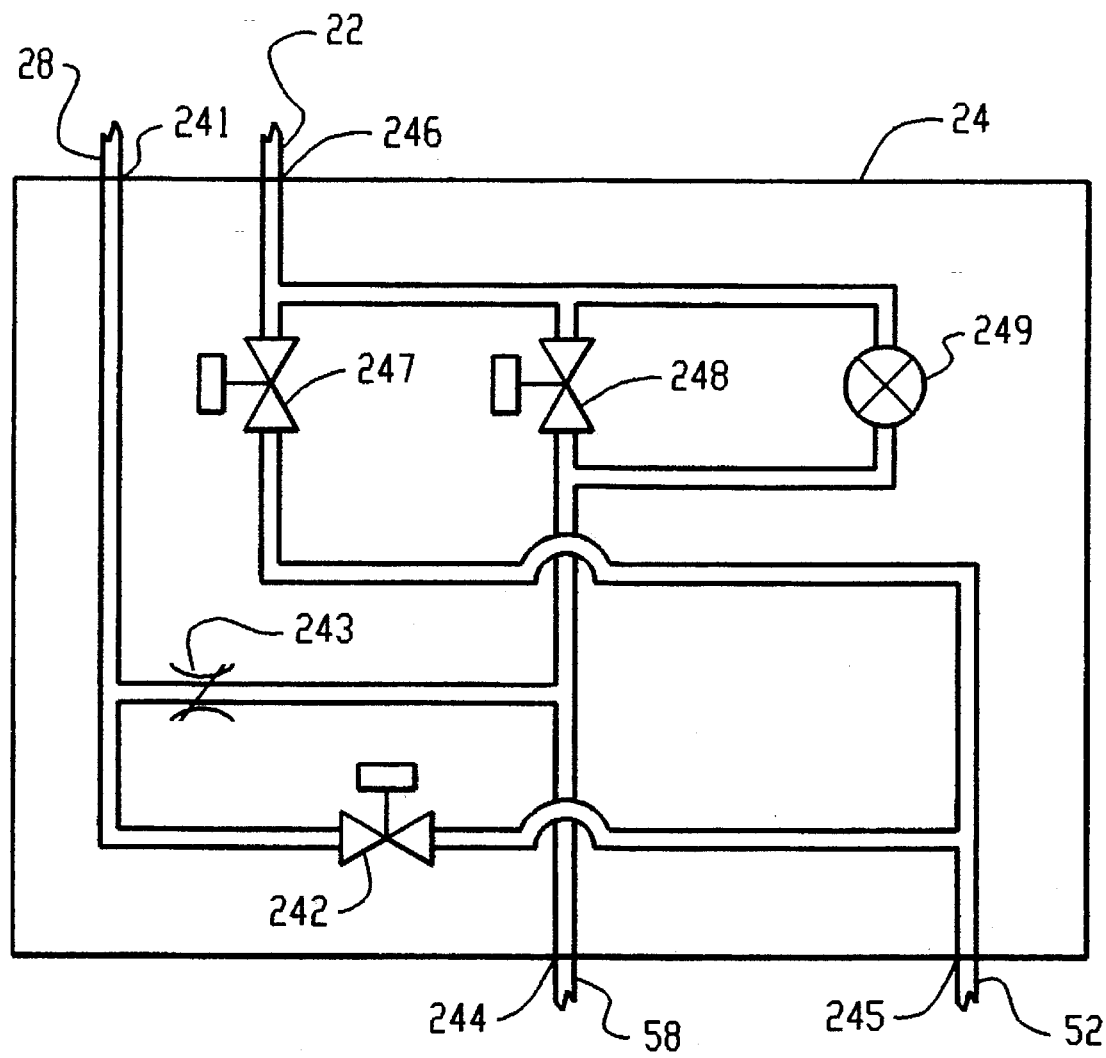
FIG. 2 is a schematic diagram of an exhaust manifold component shown in FIG. 1.

A schematic diagram of exhaust manifold 24 is depicted in FIG. 2. Entrance port 241 receives steam exiting the door seal activation space through conduit 28. Steam from port 241 flows through flow control valve 243 when solenoid valve 242 is closed. The steam flow through valve 243 is the bleed stream from the door seal activation space. Flow control valve 243 is always open. Steam flows through valve 243 and out of the exhaust manifold through exit port 244 when the door seal is activated.

Entrance port 246 receives drainage exiting the sterilization chamber through conduit 22. During a fast exhaust procedure, this stream flows through open solenoid valve 247 and exits exhaust manifold 24 through exit port 245. During a slow exhaust procedure, this stream passes through open solenoid valve 248 and exits exhaust manifold 24 through exit port 244. Valve 248 is normally in an open position, while all other solenoid valves of the sterilizer plumbing system are normally closed unless activated by the controller. It will be appreciated that the stream from the chamber drain and the stream from the door seal activation space are in sufficient proximity within the exhaust manifold to cause the transfer of heat from the door seal activation space stream to the drain stream. Steam trap 249 allows condensed steam to pass through it.

Figure 3:
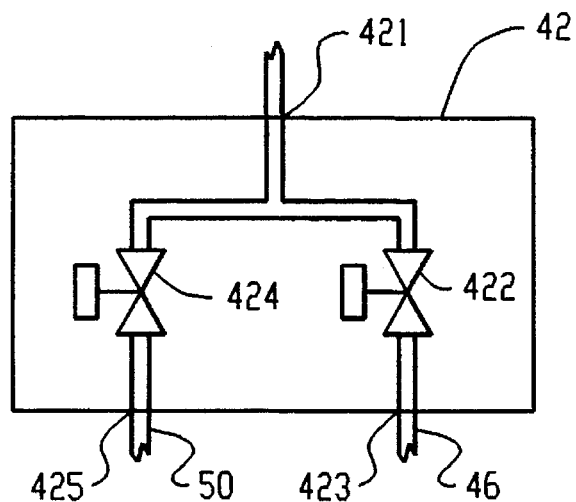
FIG. 3 is a schematic diagram of a water manifold component shown in FIG. 1.

FIG. 3 is a schematic diagram of water manifold 42. Water from an appropriate supply enters the manifold through entrance port 421. This stream can flow through open solenoid valve 422, exiting through exit port 423, and through open solenoid valve 424, exiting through exit port 425.

Figure 4:
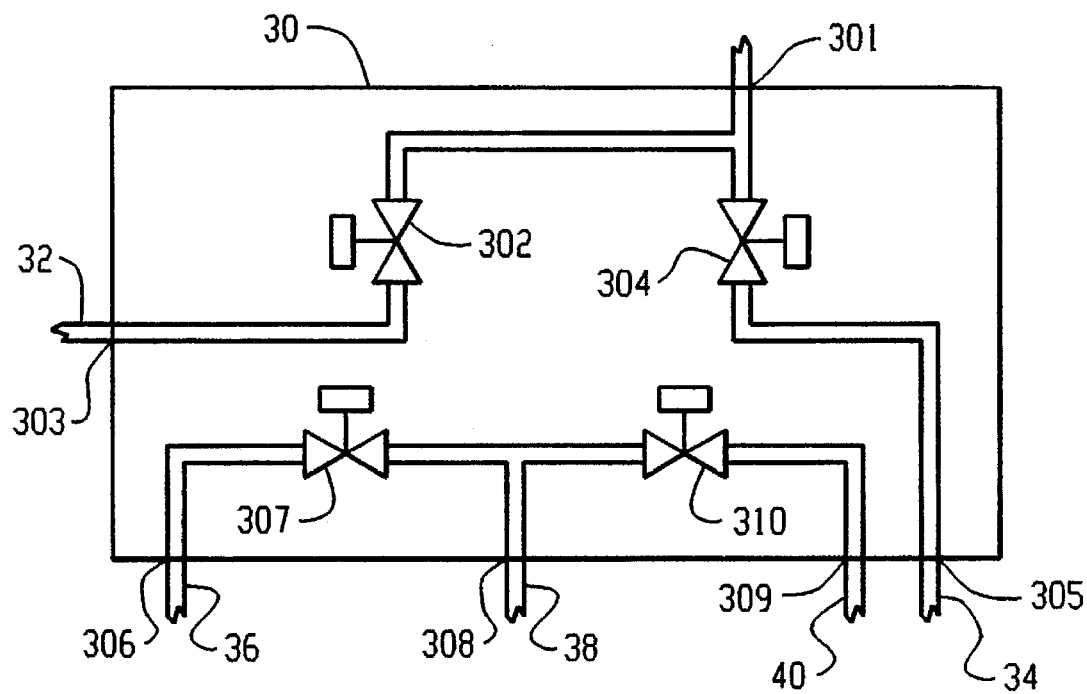
FIG. 4 is a schematic diagram of a steam manifold component shown in FIG. 1.

FIG. 4 is a schematic diagram of steam manifold 30. Steam is supplied to the manifold through entrance port 301. Steam to be supplied to the door seal 26 passes through solenoid valve 302 and exits the manifold through exit port 303. Steam to be supplied to the jacket 18 passes through solenoid valve 304 and exits the manifold through exit port 305. Steam to be supplied to the chamber 10 first enters the jacket 18 and from the jacket passes through conduit 36 to entrance port 306 of the steam manifold 30. The steam then passes through solenoid valve 307, exits the manifold through exit port 308 and enters the chamber 10 through conduit 38. Air is supplied to the chamber 10 through entrance port 309 of the steam supply manifold 30, where it passes through solenoid valve 310 and then exits the manifold through exit port 308.

The sterilizer apparatus of this invention can be used in a variety of sterilization cycles. For sterilization of liquids, including agar, a liquid cycle as discussed below, characterized by a slow exhaust and resulting gradual change in temperature, may be utilized to reduce volatility of the liquid and avoid breakage of any glass containers in which the liquid may be stored. For instrument sets wrapped in porous material and smaller textile packages, it may be desirable to pump the entrapped air out of the packs prior to the actual sterilization. A pressure-vacuum cycle as discussed below, characterized by alternatively pressurizing and evacuating the chamber to pump this air out of the packaging prior to actual sterilization, may be used. For unwrapped instruments and glassware, and larger textile packages, a gravity cycle as discussed below and characterized by a longer sterilization period and a drying period under vacuum may be used.

After the articles to be sterilized are place within chamber 10 and door 16 is closed and locked into position, the sterilization cycle is initiated by activating the door seal 26. Activation of the door seal is the first step in any of the sterilization cycles discussed herein. The first step in activating the door seal 26 is to purge the door seal activation space by alternatively opening and closing solenoid valve 302 in the steam manifold 30 to pulse steam through the door seal activation space. The steam flowing through the door seal activation space during the seal purge is exhausted through conduit 28 to the entrance port 241 of exhaust manifold 24. Steam entering the exhaust manifold 24 at port 241 during the purge of the door seal activation space passes through solenoid valve 242 and exits the exhaust manifold 24 through port 245. The exhaust steam then passes through heat exchanger 48 and vacuum water ejector 44 where it is condensed prior to discharge through discharge outlet 56.

Once the door seal activation space is purged, it is pressurized by closing valve 242, until sufficient pressure within the door seal activation space causes the door seal 26 to move against the door 16 and seal the opening between the first end 12 of the chamber 10 and the door 16. Steam exiting the door seal activation space through conduit 28 enters the exhaust manifold 24 through port 241 and flows through flow control valve 243 to create a constant slow flow, or bleed, of steam through the exhaust manifold 24. A significant feature of this invention is that this steam bleed through the exhaust manifold 24 from the door seal activation space continues throughout the sterilization cycle, until the door seal 26 is retracted. This constant steam bleed throughout the cycle maintains an elevated temperature within the exhaust manifold 24, where drainage from the chamber 10 is also directed from chamber evacuation opening 20. The maintenance of an elevated temperature within the exhaust manifold throughout the sterilization cycle prevents any spill within the chamber 10 from solidifying downstream from the chamber evacuation opening 20.

During the door seal activation step, steam is introduced into the jacket 18 through solenoid valve 304 in steam manifold 30. Steam passes through valve 304, exits the steam supply manifold through exit port 305 and enters jacket 18 through conduit 34. Water is supplied to the water manifold 42 at entrance port 421, and passes through solenoid valve 422, exiting the manifold at exit port 423 into conduit 46 where the water flows to the vacuum water ejector 44.

Any cycle described herein also requires the chamber 10 to be purged prior to the actual sterilization. The chamber is purged by activating valve 307 in steam manifold 30 to allow steam to enter the chamber 10. Valve 247 in the exhaust manifold 24 is activated for fast exhaust of the chamber steam. Valve 424 is activated to supply water to the heat exchanger 48, while valve 422 may pulse on and off to aid in maintaining the temperature of the discharge stream.

Once the door seal 26 is activated and the chamber 10 has been purged, the steps associated with the different cycles varies.

The next step in the liquid sterilization cycle following the door seal 26 activation and the chamber 10 purge, is charging the chamber 10. Steam to the jacket 18 is supplied through valve 304, which valve will alternatively open and close as determined by the controller in the event the pressure in the chamber exceeds a predetermined value. Valve 247 which permits exhaust from the chamber 10 will be closed, as will valve 424 which permits water to flow to the heat exchanger 48. Steam to the chamber will be provided through valve 307, and steam for the door seal 26 continues through valve 302. Cooling water is provided to the discharge stream through the intermittent activation of valve 422. Charging continues in this manner until the desired sterilization temperature within the chamber is met.

The sterilization step then commences. Steam to the jacket 18 is provided through the intermittent activation of valve 304 to maintain the sterilization temperature set point. Steam to the chamber 10 and to the door seal 18 continues to be supplied. Water to the vacuum water ejector 44 is supplied intermittently to maintain the effluent stream temperature. This step is continued until the preselected sterilization time has been reached.

A slow exhaust step commences with the intermittent activation of valves 247 and 248 to exhaust the chamber 10 at a predetermined rate. Steam for the door seal 26 continues, while steam to the jacket 18 is discontinued. Valve 422 is activated to pull the chamber 10 to a predetermined vacuum at a predetermined withdrawal rate controlled by the intermittent activation of valve 247. Air is then introduced into the chamber 10 through entrance port 309 of the steam supply manifold 30 and through solenoid valve 310, exiting the manifold at exit port 308 and into the chamber 10 through conduit 38. The chamber exhaust valves 247 and 248 are closed to build pressure within the chamber.

The door seal 26 is then retracted. Steam to the door seal activation space 26 is discontinued through valve 302, and the seal exhaust valve 242 is activated. Once the pressure to the door seal activation space falls below a predetermined value, a vacuum is drawn by activating valve 422 until a predetermined vacuum is reached. The cycle then proceeds to the vapor removal step, where a mechanical solenoid (not shown) is activated to push open the door 16 allowing any vapors within the chamber to escape. The door seal exhaust valve 242 will remain open. The air supply valve 310 is closed, and the vacuum is discontinued by closing valve 422. In the final step of the liquid sterilization cycle, steam is intermittently supplied to the jacket 18 to maintain a predetermined temperature. It can be seen that the steam bleed from the door seal activation space continues to flow through the exhaust manifold throughout the sterilization cycle whenever steam is being supplied for the door seal.

The gravity cycle is the same as the liquid cycle described above through the sterilization step. A fast exhaust step commences with the activation of valve 424 for cooling water and valve 247 for draining the chamber 10. Steam to the chamber is discontinued through valve 307. Steam for the door seal 26 continues through valve 302. Cooling water to the ejector 44 through valve 422 and steam to the jacket 18 through valve 304 are intermittently supplied to control the discharge stream and jacket temperatures. The next step, vacuum drying, is initiated by discontinuing the cooling water through 424, and activating valve 422 to draw a vacuum. Air is admitted into the chamber through valve 310 after the vacuum dry step, with cooling water through 422 and steam to the jacket 18 intermittently supplied to control the temperature of the discharge stream and the jacket 18. The door seal 26 is then retracted by discontinuing steam through valve 302. Vacuum cooling water through valve 422 and door seal exhaust valve 242 will be activated. When the chamber 10 reaches atmospheric pressure, the door 16 can be opened. Steam can continue to be supplied intermittently to jacket 18 to maintain a predetermined temperature, with cooling water through valve 422 to control the discharge stream temperature. It can again be appreciated that the steam bleed from the door seal activation space continues to flow through the exhaust manifold 24 throughout the sterilization cycle whenever steam is being supplied for the door seal.

The pressure-vacuum cycle is initiated with the door seal activation step followed by the chamber purge step as described above. The cycle then proceeds to a pulse step to draw a vacuum, by discontinuing steam to the chamber through valve 307. Cooling water to the vacuum water ejector is supplied through valve 422, while steam to the jacket 18 is intermittent to control the jacket temperature. After a predetermined vacuum is reached, the next step pressurizes the chamber 10 by closing the fast chamber exhaust valve 247 and supplying steam to the jacket 18 and chamber 10 through valves 304 and 307 respectively. Additional combinations of pulse steps followed by pressure steps can be utilized depending on the type of material to be sterilized, as known in the art. The final pulse step is followed by the chamber charge step as set forth in the liquid cycle and the gravity cycle described above. The rest of this sterilization cycle proceeds as the gravity cycle described above. It can again be appreciated that the steam bleed from the door seal activation space continues to flow through the exhaust manifold 24 throughout the sterilization cycle whenever steam is being supplied for the door seal.

It is to be understood that the time period for each step described in the sterilization cycles discussed herein is a function of the design of the sterilization apparatus and the articles to be sterilized, as known in the art. Further, the appropriate pressures and temperatures for each step described in the sterilization cycles discussed herein are also functions of the sterilization apparatus design and the articles to be sterilized, as known in the art.

Figure 5:
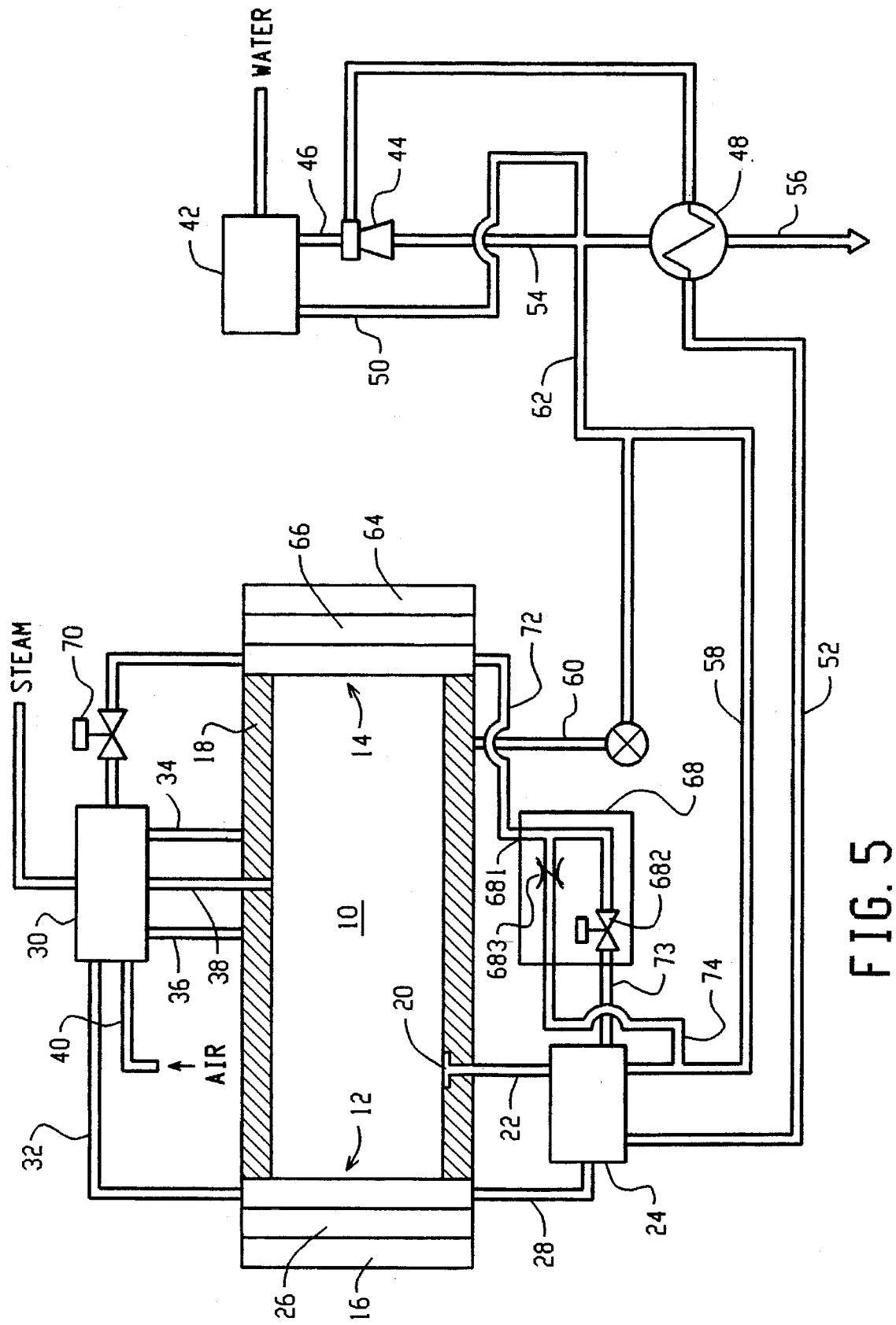
FIG. 5 is a schematic diagram of a second embodiment of a sterilizing apparatus according to this invention.

It should be appreciated that another embodiment of the invention described herein is a sterilization apparatus with a door on each of the two ends of the sterilization chamber. Such an embodiment is useful where materials to be sterilized are placed within the chamber through one door, while the second door serves to remove the materials after sterilization is complete. FIG. 5 is a schematic diagram of an embodiment of a sterilizing apparatus according to this invention with a door 16 at the first end 12 and a door 64 at the second end 14 of the sterilizing chamber 10. This embodiment includes a second door seal 66 and a double door manifold 68. Steam is supplied to the second door seal activation space through solenoid valve 70. The steam exiting the second door seal activation space flows through conduit 72 into the entrance port 681 of the double door manifold. Steam is not supplied to the second door seal when the second door seal 66 is not activated, and solenoid valve 682 remains open as a vent to the exhaust manifold 24 by way of conduit 73. When the second door seal 66 is activated, the steam bleed from the second door seal activation space is directed through flow control valve 683 and out the double door manifold into conduit 74.

The cycles described herein are easily adapted to a multiple door embodiment. Whenever the door seal exhaust valve 242 is activated in the single door embodiment, the door seal exhaust valve 682 would also be activated in the double door embodiment during the sterilization cycles described herein. Further, whenever steam is supplied to the first door seal activation space through valve 302, valve 70 is also activated in the double door embodiment during the sterilization cycles described herein.

As used herein, the term "connecting" includes direct connection and indirect connection.

What we claim is:

1. A sterilizing apparatus, comprising:

a sterilizing chamber connected to a source of sterilant and having a chamber drain, the sterilizing chamber having been utilized to sterilize agar;

a discharge outlet downstream of the chamber drain;

a first conduit connecting the chamber drain to the discharge outlet;

liquid agar contained in the first conduit;

the sterilizing chamber further having a door for opening and closing the chamber, the door comprising a door seal and a door seal activation space positioned between the door seal and the chamber said door seal activation space connected to a source of heated fluid;

a heated fluid within the door seal activation space at a pressure sufficient to activate the door seal to sealingly engage the door and the chamber;

a second conduit connecting the door seal activation space to the discharge outlet, wherein the heated fluid is also present within the second conduit; and an exhaust manifold positioned between the chamber drain and the discharge outlet and between the door seal activation space and the discharge outlet, the manifold comprising the first and second conduits extending therethrough;

wherein the exhaust manifold is constructed of a suitable material to allow the transfer of sufficient heat from the heated fluid in the second conduit to the liquid agar in the first conduit to maintain the temperature of the liquid agar in excess of 45°–50° C. and thereby prevent solidification of the agar prior to the discharge of the liquid agar from the discharge outlet.

2. The sterilizing apparatus of claim 1, wherein the heated fluid is a vapor, the apparatus further comprising:

a vapor supply manifold comprising
a vapor inlet port to receive vapor from the source of heated fluid, wherein the source of heated fluid is the same as the source of sterilant,
a first vapor exit port to direct vapor to said sterilizing chamber,
a conduit connecting said vapor inlet port and said first vapor exit port,
a valve positioned between said inlet port and said first vapor exit port for controlling the flow of vapor to said sterilizing chamber,
a second vapor exit port to direct vapor to said door seal activation space,
a conduit connecting said vapor inlet port and said second vapor exit port,
a valve positioned between said inlet port and said second vapor exit port for controlling the flow of vapor to said door seal activation space;
a conduit connecting said first vapor exit port and said sterilizing chamber; and
a conduit connecting said second vapor exit port and said door seal activation space.

3. A sterilizing apparatus, comprising:

a sterilizing chamber connected to a source of sterilant and having a chamber drain;

a discharge outlet downstream of the drain;

a door connected to said chamber for opening and closing said chamber;

a door seal activation space comprising a door seal fluid, wherein a door seal is capable of being activated by pressure from the introduction of the door seal fluid into the door seal activation space causing said door seal to sealingly engage said door and said chamber; and an exhaust manifold positioned between said drain and said discharge outlet and between said door seal activation space and said discharge outlet, and comprising a first inlet port connected to said drain to receive an exit stream flow from said chamber, a first exit port connected to said discharge outlet, a conduit connecting said first inlet port and said first exit port, a second inlet port connected to said door seal activation space to receive an exit stream flow of said door seal fluid, a second exit port connected to said discharge outlet, a conduit connecting said second inlet port and said second exit port, a valve positioned between said first inlet port and said first exit port for controlling the exit stream flow from said chamber, a valve positioned between said second inlet port and said second exit port for controlling the exit stream flow of said door seal fluid.

4. The sterilizing apparatus of claim 3, further comprising:

cooling means positioned between said exhaust manifold and said discharge outlet for cooling said exit streams from said door seal activation space and from said chamber;

a water supply manifold comprising
a water inlet port to receive water,
a water outlet port to distribute water to said cooling means,
a conduit connecting said water inlet port and said water outlet ports,
a valve positioned between said water inlet port and said water outlet port for controlling the flow of water to said cooling means;
a conduit connecting said water outlet port and said cooling means.

5. A sterilizing apparatus, comprising:

a sterilizing chamber connected to a source of sterilant vapor and having a chamber drain;

a discharge outlet downstream of the drain;

a door connected to said chamber for opening and closing said chamber;

a door seal capable of being activated by pressure from the introduction of the vapor into a door seal activation space causing said door seal to sealingly engage said door and said chamber; and a vapor supply manifold comprising
a vapor inlet port to receive vapor from then source of sterilant vapor,
a first vapor exit port to direct vapor to said sterilizing chamber,
a conduit connecting said vapor inlet port and said first vapor exit port,
a valve positioned between said inlet port and said first vapor exit port for controlling the flow of vapor to said sterilizing chamber,
a second vapor exit port to direct vapor to said door seal activation space,
a conduit connecting said vapor inlet port and said second vapor exit port,
a valve positioned between said inlet port and said second vapor exit port for controlling the flow of vapor to said door seal activation space;
a conduit connecting said first vapor exit port and said sterilizing chamber; and
a conduit connecting said second vapor exit port and said door seal activation space.

6. A method for preventing blockage from the solidification of liquid agar in sterilizer plumbing downstream from a sterilizing chamber, comprising the steps of:

providing a sterilizer having a sterilizing chamber, a chamber drain, a discharge outlet downstream from the drain, and a first conduit connecting the drain and the discharge outlet, the sterilizing chamber having been utilized to sterilize agar and the first conduit containing liquid agar;

heating the liquid agar in the first conduit so that the temperature of the liquid agar does not fall below 45°–50° C.; and discharging the heated liquid agar from the discharge outlet.

7. The method of claim 6, wherein the sterilizing chamber further has a door for opening and closing the chamber, the door comprising a door seal and a door seal activation space positioned between the door seal and the chamber, and the method further comprises the steps of:

provides an exhaust manifold positioned between the drain and the discharge outlet and between the door seal activation space and the discharge outlet, and a second conduit connecting the door seal activation space and the discharge outlet, the manifold comprising the first and second conduits extending therethrough;

providing a heated fluid in the door seal activation space; and flowing the heated fluid into the second conduit, wherein said flowing allows the transfer in the exhaust manifold of sufficient heat from the heated fluid in the second conduit to the liquid agar in the first conduit to prevent the solidification of the agar prior to discharging the liquid agar from the discharge outlet.

* * * * *